United States Patent [19]

Jacobs

[11] 4,418,226

[45] Nov. 29, 1983

[54] PROCESS FOR REFINING WASTE LIQUOR

[75] Inventor: Martin J. Jacobs, Terre Haute, Ind.

[73] Assignee: International Minerals & Chemical Corp., Terre Haute, Ind.

[21] Appl. No.: 432,602

[22] Filed: Oct. 4, 1982

[51] Int. Cl.$^3$ .................... C07C 31/24; C07C 29/86
[52] U.S. Cl. ............................................... 568/854
[58] Field of Search ...................................... 568/854

[56] References Cited

U.S. PATENT DOCUMENTS

| | | | |
|---|---|---|---|
| 2,304,985 | 12/1942 | Wyler | 568/854 |
| 3,082,259 | 3/1963 | Bauer et al. | 568/854 |
| 3,097,245 | 7/1963 | Russell et al. | 568/854 |
| 3,179,704 | 4/1965 | Leonard | 568/854 |
| 3,766,277 | 10/1973 | Duey et al. | 260/637 P |
| 4,328,366 | 5/1982 | Winslow et al. | 562/513 |

FOREIGN PATENT DOCUMENTS 224475  1/1959  Australia ........................ 568/854

OTHER PUBLICATIONS

Encyclopaedia of Chemical Technology, Kirk-Othmer, vol. I, pp. 778–789.

*Primary Examiner*—J. E. Evans
*Attorney, Agent, or Firm*—Robert H. Dewey

[57] ABSTRACT

Aqueous mother liquor from which pentaerythritol has been removed by crystallization is extracted with tetrahydrofuran to remove formals, and the raffinate comprising pentaerythritol is recycled to the crystallization process.

3 Claims, No Drawings

PROCESS FOR REFINING WASTE LIQUOR

This invention relates to a process for refining a waste liquor. In a particular aspect this invention relates to separation of components from a waste liquor.

Pentaerythritol is produced by reacting formaldehyde with acetaldehyde in aqueous solution in the presence of an alkaline catalyst, e.g. an alkali or alkaline earth hydroxide, usually sodium hydroxide. Also, it is known to use other aldehydes, such as β-hydroxypropionaldehyde, acrolein, acetaldol and paraldehyde in the reaction.

There are several by-products formed in this process. Principally, there are formed a salt of an organic acid (e.g. sodium formate when formaldehyde and sodium hydroxide are used in the process) and dipentaerythritol, both of which are marketable items; in addition cyclic pentaerythritol monoformal, bispentaerythritol monoformal, and unidentified compounds are formed.

Sodium formate and pentaerythritol (PE) are recovered from the reaction by crystallization and concentration. Generally about three crops of PE are taken. The mother liquor from the third crystallization is usually discarded because the cyclic and bis formals and unidentified compounds become troublesome (although it is known to hydrolyze the formals in acid medium and recover additional PE and formaldehyde). This waste mother liquor still contains significant amounts of sodium formate, PE and dipentaerythritol (di-PE) which could be recycled and recovered were it not for the undesirable substances present.

SUMMARY OF THE INVENTION

It is an object of this invention to provide a process for refining PE waste liquor.

It is another object of this invention to provide a process for the separation of components of waste liquor for recovery of marketable constituents.

Other objects of this invention will be apparent to those skilled in the art from the disclosure herein.

It is the discovery of this invention to provide a process for the purification of PE waste liquor by selective solvent extraction with tetrahydrofuran.

DETAILED DISCUSSION

According to the process of the present invention, the PE waste liquor is filtered to remove any suspended solids and then is extracted with tetrahydrofuran (THF) whereby the cyclic PE and bis PE formals are selectively extracted in the THF while the PE, di-PE and sodium formate remain principally in the aqueous raffinate. The latter is then recycled to the crystallization steps to recover additional amounts of dissolved values. Tetrahydrofuran is recovered from the extract for reuse, e.g. by distillation as the water azeotrope. The remainder contains polyol values which are useful for resin synthesis and can be marketed as is, or it can be discarded. Although tetrahydrofuran is soluble in water, it is practically insoluble in the waste liquor because of the high solids content, which minimizes the solubility of tetrahydrofuran.

The water content of the waste liquor is important, though not critical. It should be sufficiently high that no precipitation of solids occurs during the extraction step, yet if too high, the tetrahydrofuran dissolves partially or wholly in the waste liquor and the process becomes inefficient or entirely inoperable. Also, it is desirable to be able to use the tetrahydrofuran-water azeotrope which contains about 7% water. Waste liquor typically contains about 45–50% solids and 50–55% water. This composition can be easily extracted with the tetrahydrofuran azeotrope as well as tetrahydrofuran containing 12% water. Thus, there is considerable latitude in the permissible water content. The amount of tetrahydrofuran used, exclusive of water content, is in the range of from about one to about four parts by volume per part of waste liquor, preferably about 1.8–2:1, and a ratio of 1.9:1 is particularly preferred.

The solids portion of the waste liquor will typically have the following approximate composition:

| | |
|---|---|
| Sodium formate | 65% wt |
| Cyclic pentaerythritol monoformal | 7 |
| Pentaerythritol | 14 |
| Dipentaerythritol | 2 |
| Bispentaerythritol monoformal | 0.1 |
| Unidentified compounds | 12 |

The invention will be better understood with reference to the following examples. It is understood that the examples are intended only to illustrate the invention and it is not intended that the invention be limited thereby.

EXAMPLE 1

A supply of filtered pentaerythritol waste liquor was obtained from a production unit. It analyzed 30.2% sodium formate, 16.1% organics and 53.7% water. Of the organic fraction, about 40% was pentaerythritol (PE), 34% was unidentified, 20% was cyclic pentaerythritol monoformal (PEMF), 5% was dipentaerythritol (di-PE) and 0.4% was bis-pentaerythritol monoformal (bis-PEMF).

A Karr extraction column, manufactured by Chem-Pro Equipment Corporation, Fairfield, N.J., was used for extraction studies. The glass column, 1 in. diameter, had an effective plate height of 72" containing 66 Teflon plates spaced one inch apart. The stroke length for plate stack oscillation was set at one inch. The column was equipped with upper and lower settling stage of approximately 400 ml volume. A Cole-Parmer peristaltic pump was used for pumping solvent and waste liquor. Graduated burets were used as feed tanks and effluent was collected in graduate cylinders. The volume was measured over various time periods to determine extract and raffinate flow rates. Plate stack oscillation was manually adjusted to from 60–580 rpm to avoid flooding the column. Samples were taken after 2.5 times the system volume (1360 ml, or a total of 3400 ml) had been pumped through the column.

The feed tanks were filled with waste liquor and a mixture of 7% water and 93% by weight tetrahydrofuran, respectively (the approximate composition of the azeotrope). The waste liquor feed was adjusted to 10 ml/min and the tetrahydrofuran was fed at 18.8 ml per minute.

After extraction, it was determined that practically all of the cyclic PEMF, the bis-PEMF and about half the unknowns were in the extract and nearly all of the sodium formate, mono- and di-PE and the remainder of unknowns were in the raffinate.

EXAMPLE 2

The experiment of Example 1 was repeated in all essential details except that a mixture of 12% water and tetrahydrofuran (by weight) was used for the extraction in a ratio of 1.92 parts per part of waste liquor. Results were similar except that more mono- and di-PE were found in the extract than in Example 1.

I claim:

1. A process for the purification of pentaerythritol waste liquor resulting from the process of crystallizing pentaerythritol from the mother liquor containing it, the waste liquor comprising an aqueous solution of pentaerythritol, dipentaerythritol, sodium formate, cyclic pentaerythritol monoformal and bispentaerythritol monoformal comprising the steps of extracting the waste liquor with tetrahydrofuran in a ratio of about 1-4:1 thereby forming an extract containing most of the cyclic pentaerythritol monoformal and bispentaerythritol monoformal and a raffinate containing most of the pentaerythritol, dipentaerythritol and sodium formate and recycling the raffinate to the crystallization process.

2. The process of claim 1 wherein the tetrahydrofuran is used in a ratio of about 1.8 to 2.0 parts per part of waste liquor.

3. The process of claim 1 wherein the tetrahydrofuran is used in a ratio of about 1.9 parts per part waste liquor.

* * * * *